United States Patent [19]

Foster et al.

[11] Patent Number: 5,647,491

[45] Date of Patent: Jul. 15, 1997

[54] IV RACK

[75] Inventors: Leslie Dale Foster, Brookville; Clement J. Koerber, Batesville; John Walter Ruehl, Shelbyville, all of Ind.

[73] Assignee: Hill-Rom Company, Inc., Batesville, Ind.

[21] Appl. No.: 389,548

[22] Filed: Feb. 15, 1995

Related U.S. Application Data

[63] Continuation of Ser. No. 869,475, Apr. 15, 1992, abandoned.

[51] Int. Cl.$^6$ .................................................. A47F 5/00
[52] U.S. Cl. ........................... 211/113; 211/74; 307/150; 128/DIG. 13; 604/65; 604/246
[58] Field of Search .................................. 211/113, 74, 77; 361/334, 356; 307/150; 128/DIG. 12, DIG. 13; 604/80, 81, 246, 258, 259

[56] References Cited

U.S. PATENT DOCUMENTS

| | | |
|---|---|---|
| D. 260,816 | 9/1981 | Zissimopoulos . |
| 1,290,809 | 1/1919 | Truax . |
| 1,490,650 | 4/1924 | Wagner . |
| 2,470,524 | 5/1949 | Scudder . |
| 2,673,771 | 3/1954 | Krewson . |
| 2,696,963 | 12/1954 | Shepherd . |
| 3,139,985 | 7/1964 | Sinclair . |
| 3,552,577 | 1/1971 | Latham, Jr. et al. . |
| 3,702,940 | 11/1972 | Stewart . |
| 3,778,232 | 12/1973 | McMorrow, Jr. ............... 211/74 X |
| 4,225,104 | 9/1980 | Larson . |
| 4,262,872 | 4/1981 | Kodet . |
| 4,352,991 | 10/1982 | Kaufman . |
| 4,511,157 | 4/1985 | Wilt, Jr. . |
| 4,511,158 | 4/1985 | Varga et al. . |
| 4,513,796 | 4/1985 | Miller et al. . |
| 4,559,036 | 12/1985 | Wunsch . |
| 4,600,209 | 7/1986 | Kerr, Jr. . |
| 4,653,518 | 3/1987 | Adachi ............................. 211/89 X |
| 4,678,460 | 7/1987 | Rosner . |
| 4,712,590 | 12/1987 | Gianfilippo . |
| 4,718,892 | 1/1988 | Yung-Ho . |
| 4,720,768 | 1/1988 | Schindele . |
| 4,729,576 | 3/1988 | Roach . |
| 4,738,368 | 4/1988 | Desjardins ......................... 211/113 |
| 4,747,826 | 5/1988 | Sassano . |
| 4,795,122 | 1/1989 | Petre . |
| 4,905,944 | 3/1990 | Jost et al. . |
| 4,925,444 | 5/1990 | Orkin et al. . |
| 4,945,592 | 8/1990 | Sims et al. . |
| 4,946,439 | 8/1990 | Eggers . |
| 4,966,340 | 10/1990 | Hunter . |
| 4,993,683 | 2/1991 | Kreuzer . |
| 4,995,432 | 2/1991 | Tervamaki et al. . |
| 5,037,390 | 8/1991 | Raines et al. . |
| 5,112,019 | 5/1992 | Metzler et al. ................... 248/171 X |
| 5,167,928 | 12/1992 | Kelly et al. . |
| 5,186,337 | 2/1993 | Foster et al. . |
| 5,207,642 | 5/1993 | Orkin et al. . |

*Primary Examiner*—Robert W. Gibson, Jr.
*Attorney, Agent, or Firm*—Barnes & Thornburg

[57] ABSTRACT

An IV rack is a frame having spaced horizontal bars. IV containers are hung from the top bar. Pumps are mounted between the lower bars. Conductors and accessible contacts for the respective pumps are mounted in and form a part of the IV rack so that the pumps can be connected to a single DC power supply and a single AC power supply.

16 Claims, 1 Drawing Sheet

IV RACK

This application is a continuation of application Ser. No. 07/869,475 filed Apr. 15, 1992 now abandoned.

BACKGROUND OF THE INVENTION

This invention relates to an IV rack. The rack is generally of the type disclosed in U.S. Pat. No. 4,795,122 and copending application Ser. No. 07/524,038, filed May 16, 1990 now U.S. Pat. No. 5,117,521, both of which are incorporated herein by reference.

In critical care situations, an IV rack of the type disclosed in U.S. Pat. No. 4,795,122 is used in order to supply the patient with the multiple fluids that may be required as dictated by the patient's condition. Such fluids include heparin, nitroglycerin, antibiotics, nutrients and the like. In extreme situations, such as those involving burn patients, as many as twelve to fifteen IV infusions with twelve to fifteen pumps may be required.

Each pump is connected to an electrical outlet that provides 110 volts to drive the pumps. The pump housing contains a DC power supply that is utilized to keep the pump operating when the 110 volt AC power supply is disconnected, as, for example, when a patient is transferred from his hospital room to another location in the hospital for diagnosis or treatment.

The current hardware and practices suffer major disadvantages. The multiple conductors connecting the pumps to 110 volt AC outlets add to the general untidiness and complexity of the equipment surrounding the patient. Further, the DC power supply that is mounted in each pump housing substantially doubles the required size of the power supply and pump combination and greatly increases the weight of the combination. All of this in turn provides a practical limit for the number of pumps and power supplies to be mounted on an IV rack which must be transported with the patient from time to time.

SUMMARY OF THE INVENTION

An objective of the present invention has been to provide an IV rack for pumps and IV containers wherein the combination is greatly simplified and the weight and size reduced.

Another objective of the present invention has been to provide an improved smaller, lighter weight pump.

These objectives of the present invention have been attained by providing an IV rack wherein the electrical conductors from the power supply and contacts for the respective pumps are mounted in and become a permanent part of the IV rack. Provision is made for connecting the electrical conductors to a single AC power supply and a single DC power supply as contrasted to the multiple conductors required for separate power supplies to each pump.

Further, the pump is provided without any battery and without any conductor suitable for connection to an AC power supply. Rather, the pump is provided with electrical contacts which will mate with the contacts in the IV rack, thereby connecting the pump to the desired power supply when the pump is inserted into the rack.

In one embodiment of the invention, the auxiliary DC power supply is in the form of a battery mounted in and forming a part of the rack. In an alternative embodiment, the power supply is mounted on a care cart of the type described in copending application Ser. No. 07/524,038, and one conductor can make the connection to the IV rack from the power supply in the care cart.

The advantages of the present invention are that the invention eliminates the tangle of electrical conductors coming from a plurality of pumps mounted on the rack, that there is a reduction in the size of the pump, thereby permitting the construction of a rack of a more reasonable size, and finally, that the pump is significantly reduced in weight and hence the assembly of multiple pumps on the single rack is much lighter.

BRIEF DESCRIPTION OF THE DRAWINGS

The several objectives, features and advantages of the present invention will become more readily apparently from the following detailed description taken in conjunction with the accompanying drawing which is:

A diagrammatic view, partly in section, of an IV rack of the present invention and associated structure.

DETAILED DESCRIPTION OF THE INVENTION

Figure 1:
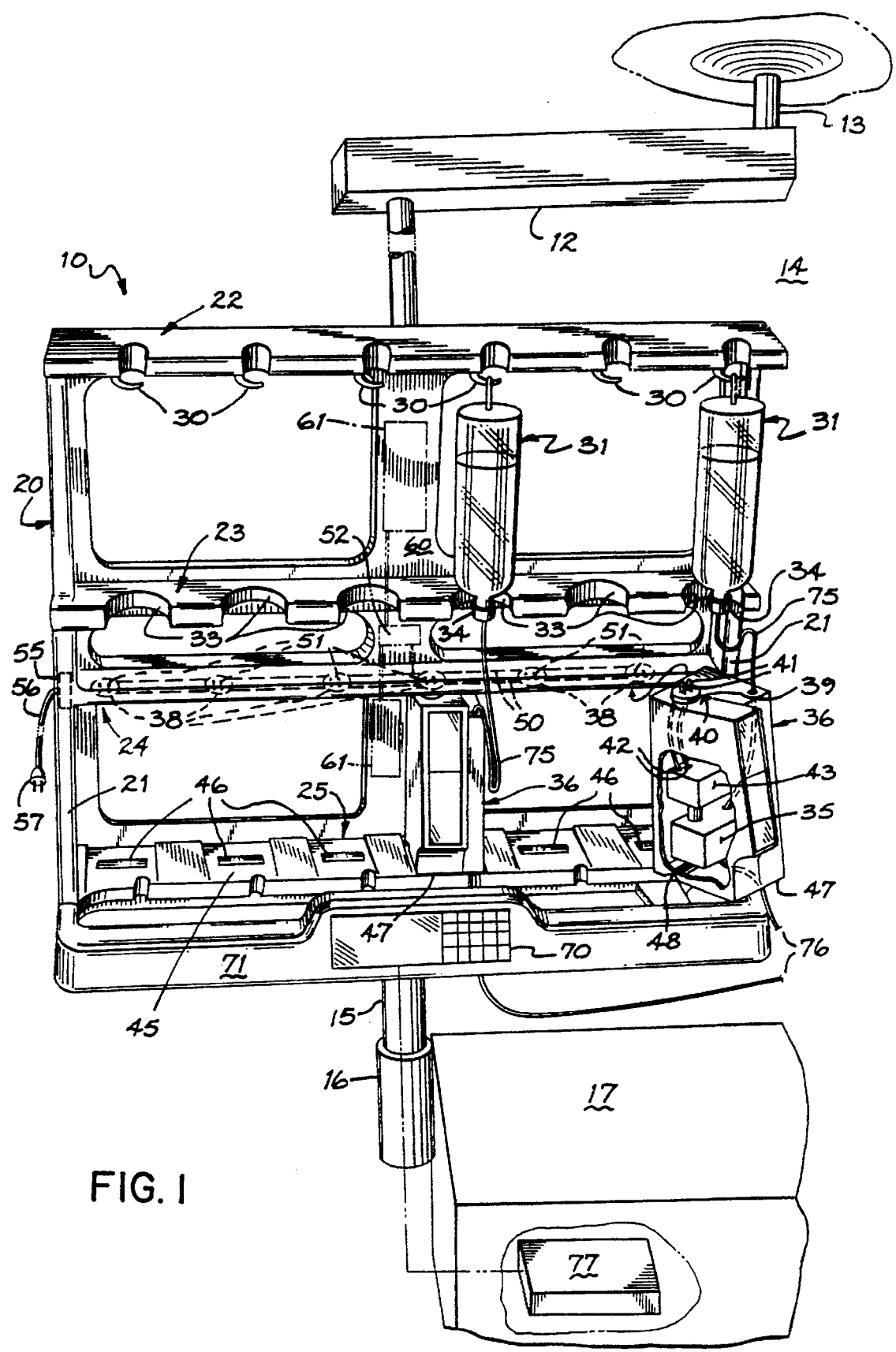

Referring to FIG. 1, there is shown an IV rack 10. It is suitable for being mounted on an arm 12 pivoted at 13 from the ceiling of a hospital room 14. The ceiling mount is generally in accordance with U.S. Pat. No. 4,795,122 which is incorporated herein by reference.

The rack also has a depending stud 15 adapted to be received in a socket 16 mounted on a care cart 17 so that the rack 10 can be released from the ceiling arm 12, mounted on the care cart 17 and transported to another destination. Preferably the care cart 17 is of the type disclosed in copending application Ser. No. 07/524,038 now U.S. Pat. No. 5,117,521. That care cart is adapted to be nested with respect to a mobile hospital bed so that the hospital bed and care cart can be moved as a unit to the patient's destination.

The IV rack has a frame 20 which includes two spaced vertical posts 21 that are interconnected by a pair of upper horizontal bars 22, 23 and lower horizontal bars 24 and 25.

The uppermost horizontal bar 22 has six hooks 30, each of which is adapted to receive a container 31 of IV solution.

Horizontal bar 23, adjacent to the horizontal bar 22, has recesses 33, each of which receives the lower end 34 of the container 31 so as to minimize the swinging of the container with respect to the rack when the rack is in transport.

The lower horizontal bars 24 and 25 cooperate to receive and fix into position six pumps 35 mounted in generally rectangular housings 36. The upper bar 24 has six receptacles or sockets 38 each of which receives a cylindrical boss 39 mounted in the upper end 40 of the housing 36. A pair of contacts 41 project from the boss 39 and are connected in the interior of the housing by leads 42 through a motor 43 which drives the pump 35.

The lower bar 25 has a horizontal platform 45 having six upwardly-projecting, shallow ribs 46. The lower surface of the housing, indicated at 47, has a corresponding recess 48 adapted to receive a rib 46. The combination of the boss 39 in the socket 38 and the boss 46 in the recess 48 securely holds the pump housing 36 on the rack.

In the horizontal bar 24 are a pair of conductors 50. The conductors 50 form a bus to which six sets of contacts 51 are mounted in and accessible through each socket 38. The contacts 51 are engaged by the contacts 41 on the pump housing 36 so as to make electrical contact therewith.

The bus 51 is connected through a rectifier 55 to a conductor 56 having a plug 57 suitable for insertion into a conventional 110 volt outlet.

The rack has a center column 60. Optionally, the center column 60 forms a housing for an auxiliary DC power supply 61 consisting of the batteries depicted in the drawing. The batteries are connected through a suitable control box 52 to the bus 50 so as to provide power to the pumps connected to the bus 50 when the AC supply is disconnected, as, for example, during transportation of the cart and patient to another destination. The batteries provide the same voltage as the rectified voltage from the AC power supply.

Optionally, each pump can have internal controls by which the frequency and quantity of the dosage of liquid from the respective IV containers can be programmed using a simple keyboard system on the pump as is presently conventional practice. Alternatively, a keyboard 70 can be mounted on a separate horizontal bar 71 on the rack and connected through suitable conductors to separate low voltage control contacts formed in the rack, as, for example, on the lower bar 25 so that connection is made when the pump is mounted on the rack.

In the operation of the invention, a plurality of IV containers 31 are mounted on the rack 10 by hanging them on the appropriate hooks 30. A pump 35 and housing 36 are mounted on the rack immediately below its respective container. Tubing 75 from the IV container is connected to the pump. Tubing 75 from the pump is connected to the patient.

The pump contacts 41 are inserted into the respective receptacle 38 so as to provide power to the motor 43 that drives the pump. The plug 57 is connected to an electrical outlet to provide rectified DC power to the bus 50.

The dosage control is programmed into the pump either by manipulating the keyboard on the pump or by manipulating the keyboard 70 depending upon which alternative is employed.

The patient is thus supplied with the various fluids from the several containers 31 and pumps 35 as needed.

In the event that the patient must be transported to another destination, the arm 12 is lowered until the stud 15 is introduced into the socket 16 of the care cart 17. Then the plug 57 is disconnected and the auxiliary DC power supply takes over to provide the continuous operation of the pumps without interruption.

As an alternative to the power supply built into the rack, which significantly adds to the weight of the rack, it is contemplated that an auxiliary DC power supply 77 would be mounted on the care cart 17. Contacts associated with the post 15 and socket 16 would make automatic connection of the bus 50 to the power supply 77 when the rack is lowered onto the care cart 17.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. Infusion apparatus comprising:

a support;

a rectangular frame adapted to receive and support containers of IV fluids and adapted to receive and support pumps for dispensing the IV fluids, said frame removably mountable to said support and being formed with an upper rectangular compartment and a lower rectangular compartment;

a plurality of accessible electrical contacts and sockets mounted in said lower compartment of said frame and spaced from said support;

said upper compartment being provided with a plurality of hooks extending from a side of the upper compartment and each hook shaded to support a container of IV fluid;

each of said sockets shaped to hold a single pump;

a plurality of passageways interconnecting the upper and lower compartments adjacent said contacts to allow for the passage of tubing between a respective IV container and its associated pump;

a conductor for connecting said contacts to a source of electrical power;

said contacts being adapted to be in close proximity to the pumps when the pumps are received on the frame such that the pumps receive electrical power from the source through said conductor and contacts.

2. The infusion apparatus of claim 1 wherein said frame includes a horizontal bar, and said frame contacts are mounted in said horizontal bar.

3. The infusion apparatus of claim 1 wherein said frame includes a pair of horizontal bars, said frame contacts are mounted in one bar of said pair of horizontal bars, and the pumps are adapted to be received between said pair of horizontal bars.

4. The infusion apparatus of claim 1 further comprising an AC power source and wherein said conductor connects said contacts to said AC power source.

5. The infusion apparatus of claim 1 further comprising a DC power source and wherein said conductor connects said contacts to said DC power source.

6. The infusion apparatus of claim 5 wherein said DC power source is a battery mounted in said frame.

7. The infusion apparatus of claim 5 wherein said DC power source is a battery mounted below said lower compartment.

8. The infusion apparatus of claim 1 wherein said frame includes a controller for controlling the pumps.

9. Infusion apparatus comprising:

a support;

a rectangular frame adapted to receive and support containers of IV fluids and adapted to receive and support pumps for dispensing the IV fluids, said frame being removably mountable to said support and being formed with an upper rectangular compartment and a lower rectangular compartment;

a plurality of accessible electrical contacts mounted in said lower rectangular compartment of said frame and spaced from said support;

a plurality of pumps mounted in said lower rectangular compartment of said frame, each pump of said plurality of pumps having electrical contacts engaging said frame electrical contacts;

a conductor for connecting said frame contacts to a source of electrical power;

said frame contacts receiving electrical power from the source through said conductor to energize said pumps through said pump contacts;

said upper compartment being provided with a plurality of hooks extending from a side of the upper rectangular compartment wherein each hook is configured to support a container of IV fluid; and a plurality of passageways between the upper and lower rectangular compartments adjacent said contacts to allow for passage of tubing between a respective IV container and assorted pump.

10. The infusion apparatus of claim 9 wherein said frame includes a horizontal bar, and said frame contacts are mounted in said horizontal bar.

11. The infusion apparatus of claim 9 wherein said frame includes a pair of horizontal bars, said frame contacts are mounted in one bar of said pair of horizontal bars, and said pumps are received between said pair of horizontal bars.

12. The infusion apparatus of claim 9 further comprising an AC power source and wherein said conductor connects said contacts to said AC power source.

13. The infusion apparatus of claim 9 further comprising a DC power source and wherein said conductor connects said contacts to said DC power source.

14. The infusion apparatus of claim 13 wherein said DC power source is a battery mounted in said frame.

15. The infusion apparatus of claim 13 wherein said DC power source is a battery mounted below said lower compartment.

16. The infusion apparatus of claim 9 wherein said frame includes a controller for controlling said pumps.

* * * * *